US005848589A

United States Patent [19]

Welnetz

[11] Patent Number: 5,848,589

[45] Date of Patent: Dec. 15, 1998

[54] ALTITUDE MASK SIMULATOR

[76] Inventor: Robert J. Welnetz, 522 Birch St., Antigo, Wis. 54409

[21] Appl. No.: 933,215

[22] Filed: Sep. 18, 1997

[51] Int. Cl.[6] .................................................. A61M 15/00

[52] U.S. Cl. ............................... 128/200.24; 128/202.11; 128/202.12; 128/205.25; 128/205.27; 128/206.12; 128/206.15; 128/206.21

[58] Field of Search ......................... 482/13; 128/200.24, 128/202.11, 202.12, 205.11, 205.25, 205.27, 206.12, 206.15, 206.21

[56] References Cited

U.S. PATENT DOCUMENTS

| | | | |
|---|---|---|---|
| 938,247 | 10/1909 | Kuhn | 482/13 |
| 4,198,213 | 4/1980 | Mannatt | 128/205.11 |
| 4,210,137 | 7/1980 | Henkin | 128/200.24 |
| 4,334,533 | 6/1982 | Henkin | 128/205.28 |
| 4,364,384 | 12/1982 | Warncke et al. | 128/204.28 |
| 4,664,108 | 5/1987 | Ansite | 128/202.26 |
| 4,823,788 | 4/1989 | Smith et al. | 128/205.24 |
| 4,844,059 | 7/1989 | Koch | 128/205.27 |
| 4,944,293 | 7/1990 | Swiatosz et al. | 128/205.24 |
| 5,158,584 | 10/1992 | Tamura | 128/205.11 |
| 5,211,728 | 5/1993 | Trimmer | 128/205.11 |
| 5,249,570 | 10/1993 | Cox | 128/206.28 |
| 5,383,448 | 1/1995 | Tkatchouk et al. | 128/205.27 |
| 5,467,764 | 11/1995 | Gamow | 128/200.24 |
| 5,643,355 | 7/1997 | Phillips et al. | 128/205.27 |
| 5,647,345 | 7/1997 | Saul | 128/200.24 |
| 5,649,533 | 7/1997 | Oren | 128/200.24 |

*Primary Examiner*—Aaron J. Lewis
*Attorney, Agent, or Firm*—Chase & Yakimo, L.C.

[57] ABSTRACT

A training mask for replicating the decrease in oxygen density and the increased breathing effort at higher altitudes. The mask has a nasal portion for covering the user's nose and a lower portion for covering the user's mouth. A peripheral edge conformable with the face forms a chamber with the user's mouth and nose contained therein. A valve-controlled air channel presents a first exterior aperture in communication with the outside ambient air and a second interior aperture positioned adjacent the user's mouth. A fibrous filter, or a plurality of such filters, are releasably engageable within the air channel. Upon inhalation the oxygen density of the ambient air, as drawn through the air channel and through the fibrous filter(s), is decreased. This decrease replicates the decrease in oxygen found in the ambient air at higher altitudes which requires the user to increase the breathing effort so as to deliver a sufficient amount of oxygen to the bloodstream. Upon exhalation the exhaled air is discharged through valve controlled exhaust ports.

11 Claims, 6 Drawing Sheets

ALTITUDE MASK SIMULATOR

BACKGROUND OF THE INVENTION

This invention pertains to a breathing apparatus and, more particularly, to a training mask capable of simulating the oxygen density of the air at higher altitudes.

It is known as the altitude increases above sea level that the oxygen concentration in the air decreases. This decrease may introduce physiological symptoms if the person is not acclimated to such an oxygen deficiency. At such increased altitudes the person must breathe more deeply to supply sufficient oxygen to the blood stream. It is known that persons, acclimated to sea level conditions, may initially experience various maladies during their initial presence at substantially higher altitudes, particularly above 7,500 feet. Such maladies include shortness of breath, headaches, dizziness, decreased endurance and the like. After a few days at the higher altitude, acclimatization usually occurs so that these symptoms will diminish, if not disappear.

Accordingly, it is desirable to provide a device that will simulate the condition of the ambient air at higher altitudes such that a user can acclimate one's self prior to entering the higher altitude. Although apparatus for simulating higher altitude conditions have been proposed, it is desirable to have an economical device which can be easily worn by a user while the user engages in various kinds and/or levels of activities.

SUMMARY OF THE INVENTION

In response thereto I have invented a mask which is worn by the user so as to enclose the user's mouth and nose in an air tight chamber. The mask restricts oxygen air intake to a single channel, the mask having additional vents for discharge of the exhaled air. The intake channel is configured to releasably receive a plurality of filters therein which requires the exertion of air inhalation by the user to be increased so as to deliver the proper amount of oxygen to the bloodstream. This increase in breathing effort simulates the increased effort of inhalation needed at higher altitudes. This replication of breathing effort will precondition the user to a diminished oxygen environment as to be presented at the higher altitude. Thus, acclimatization can be accomplished without the necessity of the user to be physically located at such an environment.

It is therefore a general object of this invention to provide a training device for simulating an ambient air environment at relatively different altitudes.

Another object of this invention is to provide a device, as aforesaid, which can be easily worn by the user while engaged in various activities.

A further object of this invention is to provide a device, as aforesaid, which regulates the breathing effort of a user required to deliver sufficient oxygen to the user's bloodstream.

Still another object of this invention is to provide a device, as aforesaid, which replicates the ambient air found at various altitudes.

A still further object of this invention is to provide a device, as aforesaid, which limits the amount of oxygen delivered to a user.

Still another object of this invention is to provide a device, as aforesaid, the device being in the form of a portable, lightweight mask for wear by the user.

Other objects and advantages of this invention will become apparent from the following description taken in connection with the accompanying drawings, wherein is set forth by way of illustration and example, a now preferred embodiment of this invention.

DESCRIPTION OF THE PREFERRED EMBODIMENT

Figure 1:
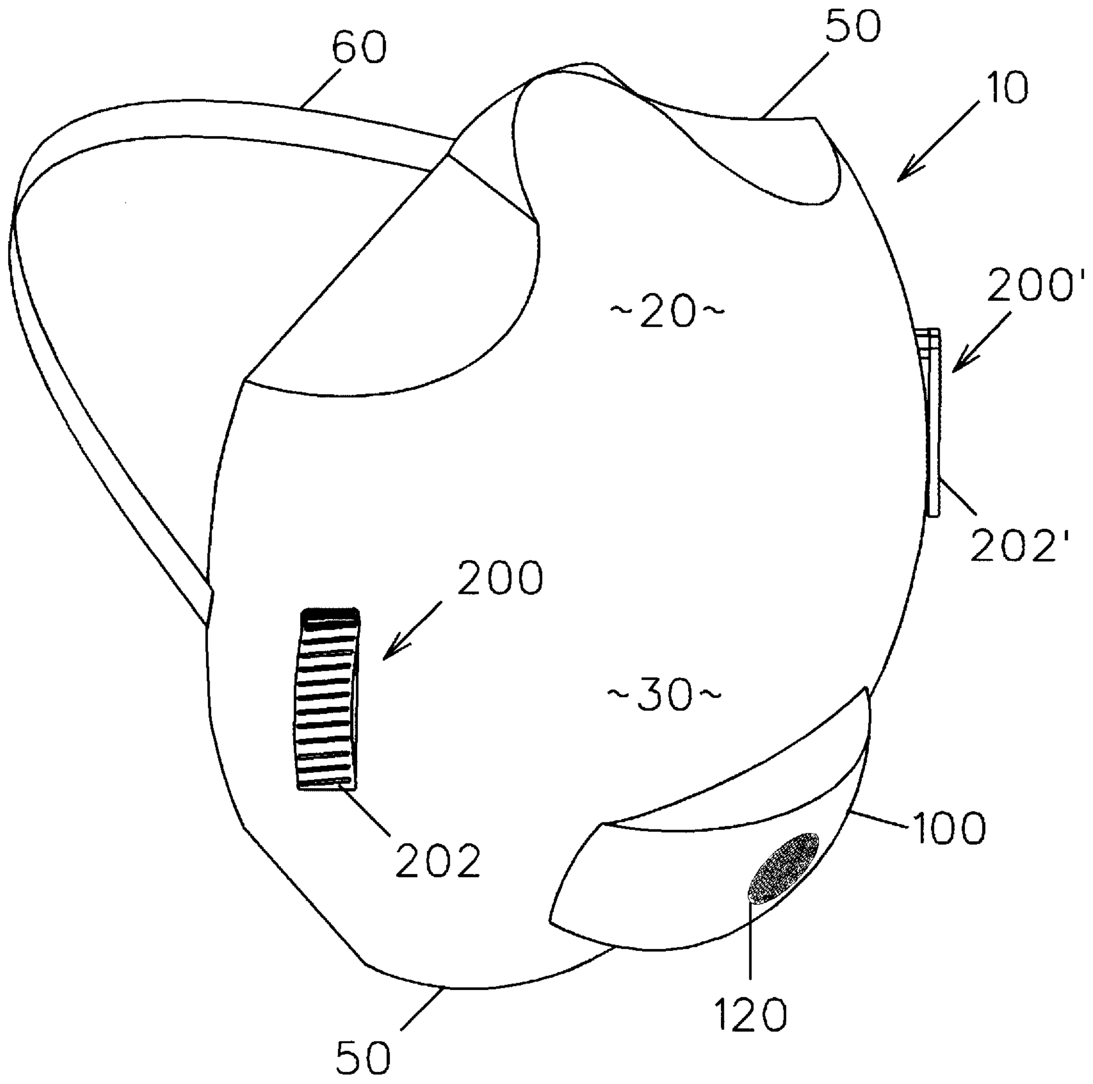
FIG. 1 is a perspective view of the mask.

Turning more particularly to the drawings, FIG. 1 shows the trainer in the form of a mask 10 preferably made of a clear plastic, the plastic having a configuration presenting a nasal area 20 and a mouth area 30 adapted to cover the nose and mouth of the user. The peripheral edges 50 of the mask 10 are preferably made of a resilient material adapted to conform to the face of the user. Strap 60 enables the mask 10 to be maintained in place on the user's face.

Figure 3:
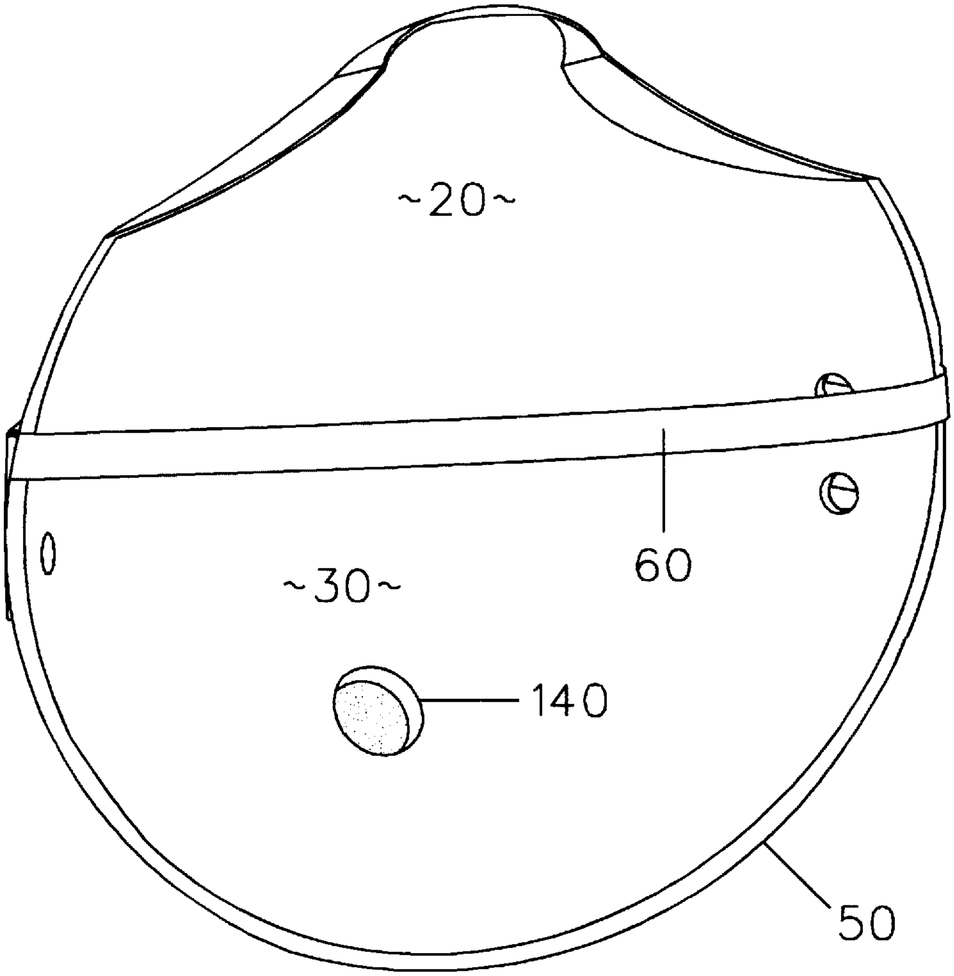
FIG. 3 is a rear view of the mask of FIG. 2.

Projecting from the front of the mask 10 at the mouth area 30 thereof is a housing 100 having a valve 150 regulated air channel 130 therein, the channel 130 presenting an exterior aperture 120 and an interior aperture 140 adjacent the user's mouth when the mask is in place. (The valve assembly 150 has been removed in FIG. 3 to show the interior of bore 130.)

Figure 2:
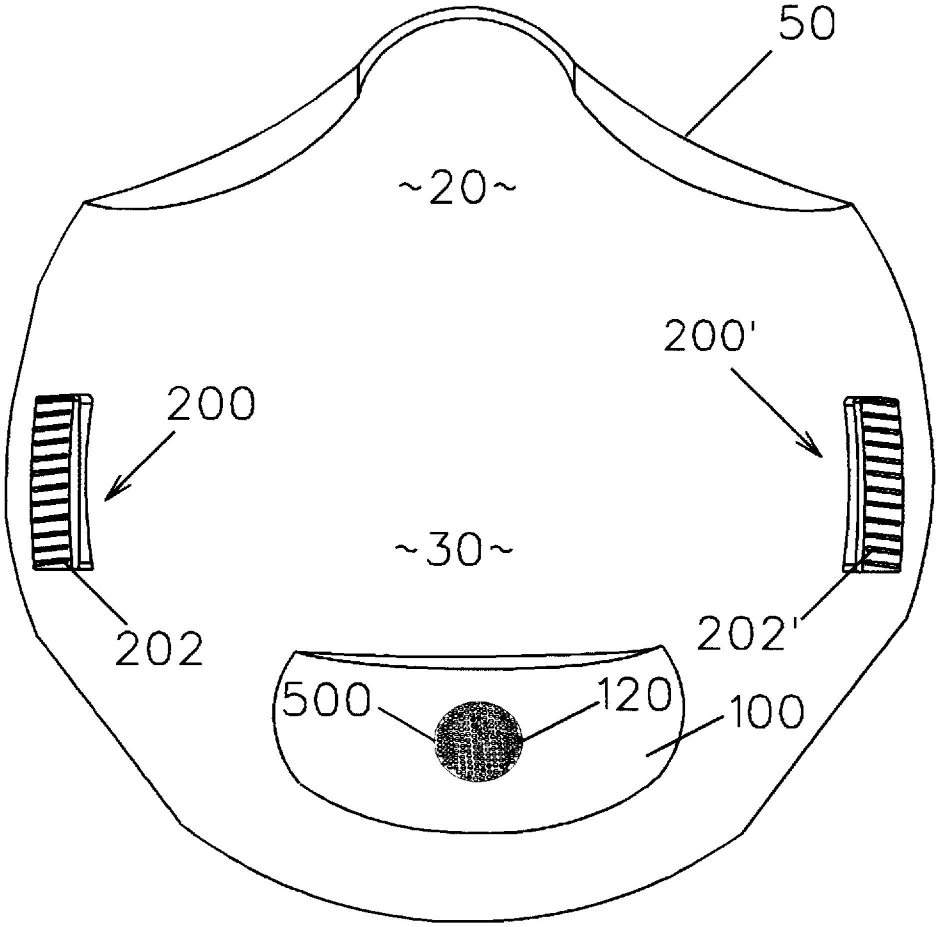
FIG. 2 is a front view of the mask of FIG. 1.
Figure 5:
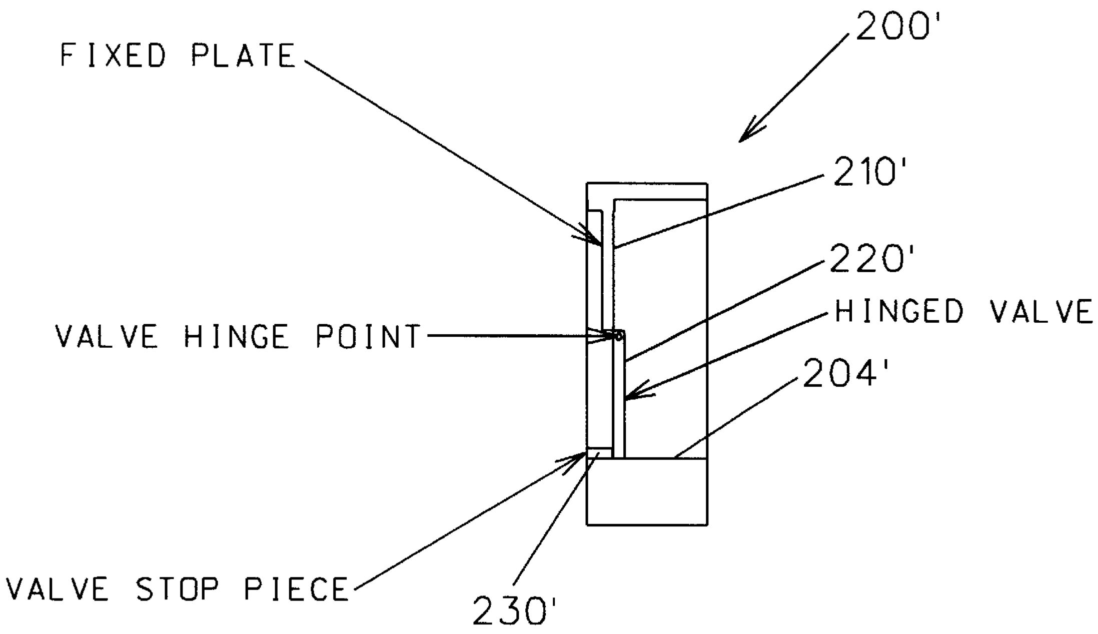
FIG. 5 is a diagrammatic view showing one of the valved exhalation ports of the mask.

Located at the opposed sides of the mask are first and second valved exhalation ports 200, 200' with port 200' being diagrammatically shown in FIG. 5. Each port is shown with a cover 202, 202' thereon (FIGS. 1, 2) to preclude entry of foreign objects therein and interference with the air exhausted from mask 10.

As shown in FIG. 5, port 200' includes a depending fixed plate 210' with a flexible flap 220' being hinged thereto. The flexible valve flap 220' conforms to and contacts the lower edge 204' of port 200'. At this spanning position the port 200' is closed to preclude passage of air therethrough. A stop lug 230', on this lower surface of port 200', bears against the valve flap 220' when valve flap 220' is at a closed position. A similar reversed construction is utilized for the port 200.

Figure 6:
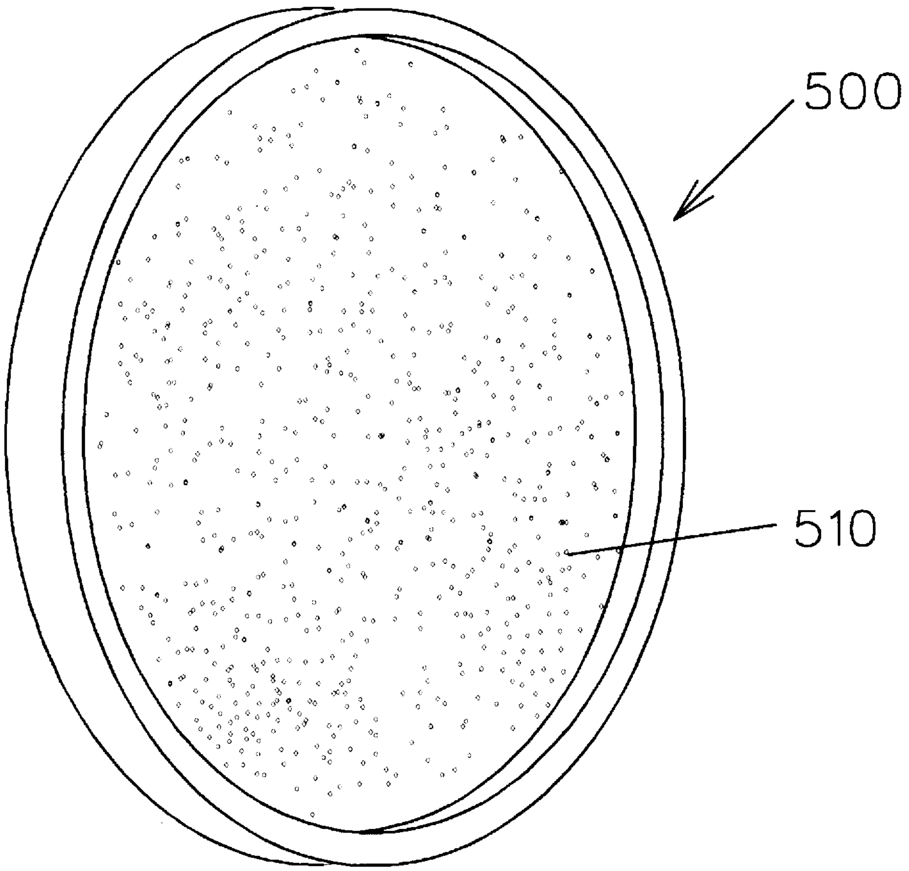
FIG. 6 is a perspective view of one of the filters, on an enlarged scale, for releasable engagement with the air inhalation channel.

The air channel 130 is capable of releasably receiving a plurality of filters 500 therein, one such filter being shown on an enlarged scale in FIG. 6. The filter 500 is made of a fibrous material 510, the density of the fibers therein being variably selected so as to variably decrease the air flow therethrough.

Figure 4:
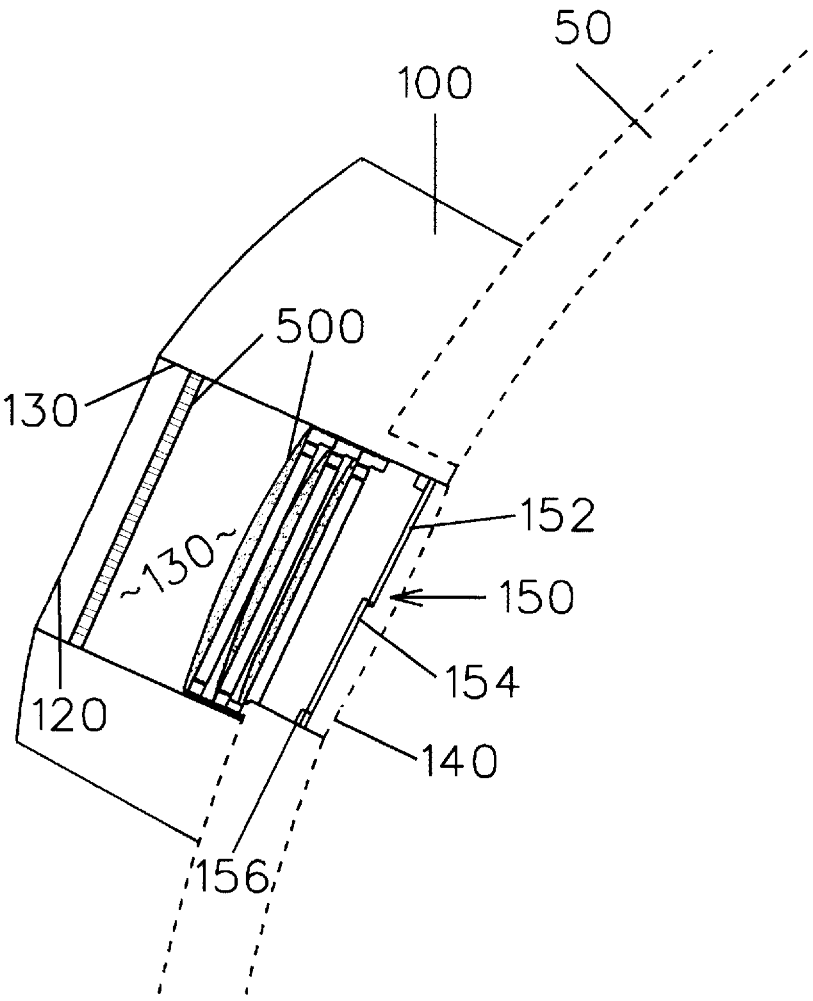
FIG. 4 is a fragmentary view of the air inhalation channel of the mask showing a plurality of filters and valve means therein.

As shown in FIG. 4, a valve assembly 150' is located at the proximal end 132 of air channel 130. The assembly 150 includes a fixed plate 152 having a flap 154 hinged thereto. Upon inhalation, flap 154 will pivot in a counterclockwise direction allowing for air to be drawn through channel 130 and into the mouth. Lug 156 limits the clockwise movement of flap 154 beyond a desired bore 130 closing position. Valve assembly 150 works in concert with assemblies 200, 200' to regulate the intake and exhaust of air relative to mask 10.

Upon placement of the mask 10 so as to cover the nose and mouth of the user, as maintained thereat by strap 60, the compliant edges 50 form a chamber with the nose and mouth therein. The intake aperture 140 of bore 130 will lie adjacent the user's mouth. The valve assemblies 150, 200, 200' are in a closed position. Upon inhalation valve assembly 150 will open. The filter(s) 500 within channel 130 impede air flow so as to decrease the amount of oxygen available to the user if the user at aperture 140. To deliver a sufficient amount of oxygen to the bloodstream of the user, the user must increase the breathing effort in a manner similar to the increased effort needed at higher altitudes. The oxygen decrease at higher altitudes as well as the required breathing effort in order to account for such an oxygen decrease are replicated. Thus the user, although at a lower altitude, can experience the decreased oxygen conditions at higher altitudes as well as the accompanying increased exertion in breathing effort.

It is understood that a selectable number of filters 500 can be placed in the air channel 130 so as to replicate successively higher altitudes. This succession of filters will replicate incrementally higher altitudes so that the user can be incrementally conditioned to such successively higher altitudes, if desired. It is also understood that the density of fibrous material 510 of the filters 500 can be varied so as to simulate various altitudes. Thus, the mask 10 can simulate a number of simulated altitudes while the user is engaged in various activities.

It is to be understood that while a certain form of this invention has been illustrated and described, it is not limited thereto except insofar as such limitations are included in the following claims and allowable functional equivalents thereof.

Having thus described the invention, what is claimed as new and desired to be secured by letters patent is as follows:

1. A training mask comprising:

a mask body comprising:

a mouth portion adapted to cover a user's mouth;

a nasal portion adapted to cover a user's nose;

a peripheral edge adapted to conform to a user's face for presenting a chamber adapted to contain a user's covered mouth and nose therein;

an air channel extending through said mask and presenting a bore with a first aperture on an outside surface of said mask and a second aperture on an inside surface of said mask;

intake valve means in said bore having a first closed position upon exhalation of air by a user and a second open position upon inhalation of a user to allow for passage of ambient air through said bore;

exhaust valve means in said mask for regulating a discharge of exhaled air of a user from the chamber and to an outside of said mask;

a filter releasably engageable within said bore, said filter having material therein adapted to impede passage of air therethrough and selectively decrease the oxygen density of the air at said second interior aperture for inhalation by a user, whereby to simulate a decrease of oxygen density in inhaled air as at a higher altitude.

2. The mask as claimed in claim 1 wherein said mask comprises a flexible material.

3. The mask as claimed in claim 2 wherein said mask comprises plastic.

4. The mask as claimed in claim 1 wherein said exhaust valve means comprises:

an exhaust bore extending through said mask;

a first flap in said exhaust bore;

a second flexible flap pivotally connected to said first flap, wherein said first and second flaps span said bore at a first position to preclude air passage therethrough, an exhalation of air moving said second flap to a second position to allow passage of said exhaled air through said exhaust bore and to an outside of said mask.

5. The mask as claimed in claim 4 further comprising a lug in said exhaust bore to preclude movement of said second flap beyond said first exhaust valve means position during inhalation by a user.

6. The mask as claimed in claim 1 wherein said intake valve means comprises:

a first flap in said air channel;

a second flexible flap pivotally connected to said first flap, said second flap biased to a position at user exhalation wherein said first and second flaps in said air channel span said bore to present said first closed position to preclude passage of air therethrough, an inhalation by a user moving said second flap to present said second open position to allow an incoming air flow through said channel, said position presenting said second open position.

7. The mask as claimed in claim 6 further comprising a lug in said air channel precluding movement of said second flap to an open position during user exhalation.

8. The mask as claimed in claim 1 further comprising a strap connected to said mask body, said strap adapted to be positioned about a head of a user to maintain said mask thereon.

9. The mask as claimed in claim 1 where said filter material comprises a fibrous material.

10. A training mask comprising:

a mask body comprising:

a mouth portion adapted to cover a user's mouth;

a nasal portion adapted to cover a user's nose;

a peripheral edge adapted to conform to a user's face for presenting a chamber adapted to contain a user's mouth and nose therein;

air inlet means extending through said mask for passage of ambient air from outside said mask and into said chamber upon inhalation by a user;

intake valve means in said inlet means having a first closed position upon exhalation of air by a user and a second open position upon inhalation of a user to regulate passage of ambient air through said inlet means;

exhaust valve means in said mask for regulating a discharge of exhaled air of a user from the chamber and to an outside of said mask;

at least one filter releasably engageable within said air inlet means, said filter having material therein adapted to selectively decrease the oxygen density of the ambient air passing therethrough for delivery to said chamber for inhalation by a user, whereby to simulate a decrease of oxygen density in the inhaled air found at a higher altitude.

11. A training mask comprising:

a body portion adapted to cover a user's mouth and nose, said mask having a peripheral edge adapted to conform to a user's face for presenting a chamber with a user's mouth and nose therein;

a bore extending through said mask and presenting an aperture on an inside surface of said mask;

intake valve means in said bore having a first closed position upon exhalation of air by a user and a second open position upon inhalation of the user to allow for a regulated passage of ambient air through said bore;

exhaust valve means in said mask for regulating a discharge of exhaled air of a user from the chamber and to an outside of said mask;

means in said bore for selectively decreasing the oxygen density of the air at said aperture upon inhalation by a user, whereby to simulate a decrease of oxygen density in the ambient air for inhalation by a user.

* * * * *

UNITED STATES PATENT AND TRADEMARK OFFICE

CERTIFICATE OF CORRECTION

PATENT NO. : 5,848,589

DATED : December 15, 1998

INVENTOR(S) : ROBERT J. WELNETZ

It is certified that error appears in the above-identified patent and that said Letters Patent is hereby corrected as shown below:

Column 4, line 56, delete "the" and substitute --a--.

Signed and Sealed this

Twenty-third Day of March, 1999

Attest:

Q. TODD DICKINSON

Attesting Officer

*Acting Commissioner of Patents and Trademarks*